(12) United States Patent
Nakagawa

(10) Patent No.: US 11,918,179 B2
(45) Date of Patent: Mar. 5, 2024

(54) IMAGE PICKUP APPARATUS FOR ENDOSCOPE, ENDOSCOPE, AND MANUFACTURING METHOD FOR IMAGE PICKUP APPARATUS FOR ENDOSCOPE

(71) Applicant: OLYMPUS CORPORATION, Tokyo (JP)

(72) Inventor: Yusuke Nakagawa, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 382 days.

(21) Appl. No.: 17/223,492

(22) Filed: Apr. 6, 2021

(65) Prior Publication Data

US 2021/0219830 A1 Jul. 22, 2021

Related U.S. Application Data

(63) Continuation of application No. PCT/JP2018/037848, filed on Oct. 11, 2018.

(51) Int. Cl.
| | |
|---|---|
| *A61B 1/00* | (2006.01) |
| *A61B 1/018* | (2006.01) |
| *A61B 1/05* | (2006.01) |
| *A61B 1/06* | (2006.01) |

(52) U.S. Cl.
CPC ...... *A61B 1/00013* (2013.01); *A61B 1/00018* (2013.01); *A61B 1/0011* (2013.01); *A61B 1/00165* (2013.01); *A61B 1/018* (2013.01); *A61B 1/05* (2013.01); *A61B 1/06* (2013.01)

(58) Field of Classification Search
CPC ............ A61B 1/00013; A61B 1/00018; A61B 1/0011; A61B 1/00165; A61B 1/018; A61B 1/05; A61B 1/06

USPC ........................................................ 600/109
See application file for complete search history.

(56) References Cited

U.S. PATENT DOCUMENTS

| | | | |
|---|---|---|---|
| 2012/0190990 A1* | 7/2012 | Ohzawa | G02B 23/26 |
| | | | 600/478 |
| 2014/0321856 A1 | 10/2014 | Saeki et al. | |
| 2016/0234408 A1* | 8/2016 | Urakawa | H04N 23/51 |
| 2018/0055342 A1* | 3/2018 | Sakai | G02B 23/2484 |

(Continued)

FOREIGN PATENT DOCUMENTS

| | | |
|---|---|---|
| JP | 2007-300460 A | 11/2007 |
| JP | 2009-122197 A | 6/2009 |
| JP | 2013-025092 A | 2/2013 |

(Continued)

OTHER PUBLICATIONS

International Search Report dated Dec. 25, 2018 issued in PCT/JP2018/037848.

*Primary Examiner* — Timothy J Neal
*Assistant Examiner* — James Edward Boice
(74) *Attorney, Agent, or Firm* — Scully, Scott, Murphy & Presser, P.C.

(57) ABSTRACT

An image pickup apparatus for endoscope includes an image sensor, a ferrule which is a rectangular parallelepiped having a front surface, a rear surface, and four side surfaces and includes insertion holes and trenches parallel to the insertion holes on respective two side surfaces orthogonal to each other among the four side surfaces, an optical element in which a light emitting region is disposed in a position opposed to the insertion holes, and optical fibers inserted into the insertion holes.

20 Claims, 15 Drawing Sheets

(56) References Cited

U.S. PATENT DOCUMENTS

2018/0239124 A1* 8/2018 Naruse .................... A61B 1/04

FOREIGN PATENT DOCUMENTS

| JP | 2013-050497 A | 3/2013 |
| JP | 2014-85639 A | 5/2014 |
| JP | 2015-68835 A | 4/2015 |
| JP | 5976769 B2 | 8/2016 |
| JP | 2018-92061 A | 6/2018 |
| WO | 2014/065436 A1 | 5/2014 |
| WO | 2016/147556 A1 | 9/2016 |
| WO | 2017/163335 A1 | 9/2017 |
| WO | 2018/105479 A1 | 6/2018 |
| WO | 2018/173323 A1 | 9/2018 |

* cited by examiner

IMAGE PICKUP APPARATUS FOR ENDOSCOPE, ENDOSCOPE, AND MANUFACTURING METHOD FOR IMAGE PICKUP APPARATUS FOR ENDOSCOPE

CROSS REFERENCE TO RELATED APPLICATION

This application is a continuation application of PCT/JP2018/037848 filed on Oct. 11, 2018, the entire contents of which are incorporated herein by this reference.

BACKGROUND OF THE INVENTION

1. Field of the Invention

The present invention relates to an image pickup apparatus for endoscope including an image sensor, an optical element, a ferrule, and an optical fiber, an endoscope including the image pickup apparatus for endoscope including the image sensor, the optical element, the ferrule, and the optical fiber, and a manufacturing method for the image pickup apparatus for endoscope including the image sensor, the optical element, the ferrule, and the optical fiber.

2. Description of the Related Art

An endoscope includes an image pickup apparatus including an image sensor such as a CCD at a distal end portion of an elongated insertion section. In recent years, use of an image sensor having a high pixel number in an endoscope has been examined. In the endoscope in which the image sensor having the high pixel number is used, since a signal amount transmitted from the image sensor to a signal processing apparatus increases, optical signal transmission via an optical fiber by an optical signal is preferable over electric signal transmission via a metal wire by an electric signal. For the optical signal transmission, an E/O type optical module (an electrooptical converter) that converts an electric signal into an optical signal and an O/E type optical module (an optoelectrical converter) that converts an optical signal into an electric signal are used.

Japanese Patent Application Laid-Open Publication No. 2013-025092 discloses an image pickup apparatus including an optical element that generates an optical signal and a ferrule including an insertion hole into which an optical fiber for transmitting the optical signal is inserted.

International Publication No. 2017/163335 discloses an image pickup apparatus manufactured by cutting an image sensor wafer along a cutting line extending across an alignment part, the image pickup apparatus having an alignment mark for electric connection on a side surface.

SUMMARY OF THE INVENTION

An image pickup apparatus for endoscope in an embodiment includes: an image sensor configured to output an image pickup signal, a ferrule that is a rectangular parallelepiped including a front surface, a rear surface on a reverse side of the front surface, and four side surfaces, and includes one or more insertion holes, a first electrode being disposed on the front surface, and one or more trenches, extending directions of which are parallel to depth directions of the insertion holes, being provided on each of two side surfaces orthogonal to each other among the four side surfaces, one or more optical elements in which a light emitting region configured to output an optical signal and an external electrode are disposed on a light emitting surface, the light emitting region is disposed in a position opposed to the insertion hole, and a driving signal based on the image pickup signal is inputted to the external electrode bonded to the first electrode, and one or more optical fibers inserted into the insertion holes.

An endoscope in an embodiment includes an image pickup apparatus for endoscope. The image pickup apparatus includes an image sensor configured to output an image pickup signal, a ferrule that is a rectangular parallelepiped including a front surface, a rear surface on a reverse side of the front surface, and four side surfaces, and includes one or more insertion holes, a first electrode, and a second electrode connected to the first electrode being disposed on the front surface, and one or more trenches, extending directions of which are parallel to depth directions of the insertion holes, being provided on each of two side surfaces orthogonal to each other among the four side surfaces, one or more optical elements in which a light emitting region configured to output an optical signal and an external electrode are disposed on a light emitting surface, the light emitting region is disposed in a position opposed to each of the insertion holes, and a driving signal based on the image pickup signal is inputted to the external electrode bonded to the first electrode, and one or more optical fibers inserted into the insertion hole.

A manufacturing method for an image pickup apparatus for endoscope in an embodiment includes simultaneously forming, in a silicon wafer, an insertion hole into which an optical fiber is inserted and one or more trench holes thereby producing a ferrule wafer, cutting the ferrule wafer along a plurality of cutting lines including a cutting line extending across the trench holes, and producing a ferrule that is a rectangular parallelepiped including a front surface, a rear surface, and four side surfaces and includes, in each of two orthogonal side surfaces of the four side surfaces, a trench having a cut surface of the trench holes as an opening, mounting an optical element, on a light emitting surface of which a light emitting region configured to output an optical signal and an external electrode are disposed, on the ferrule in a position where the light emitting region is disposed to be opposed to the insertion hole of the ferrule; and inserting the optical fiber into the insertion hole of the ferrule.

DETAILED DESCRIPTION OF THE PREFERRED EMBODIMENTS

<Endoscope System>

Figure 1:
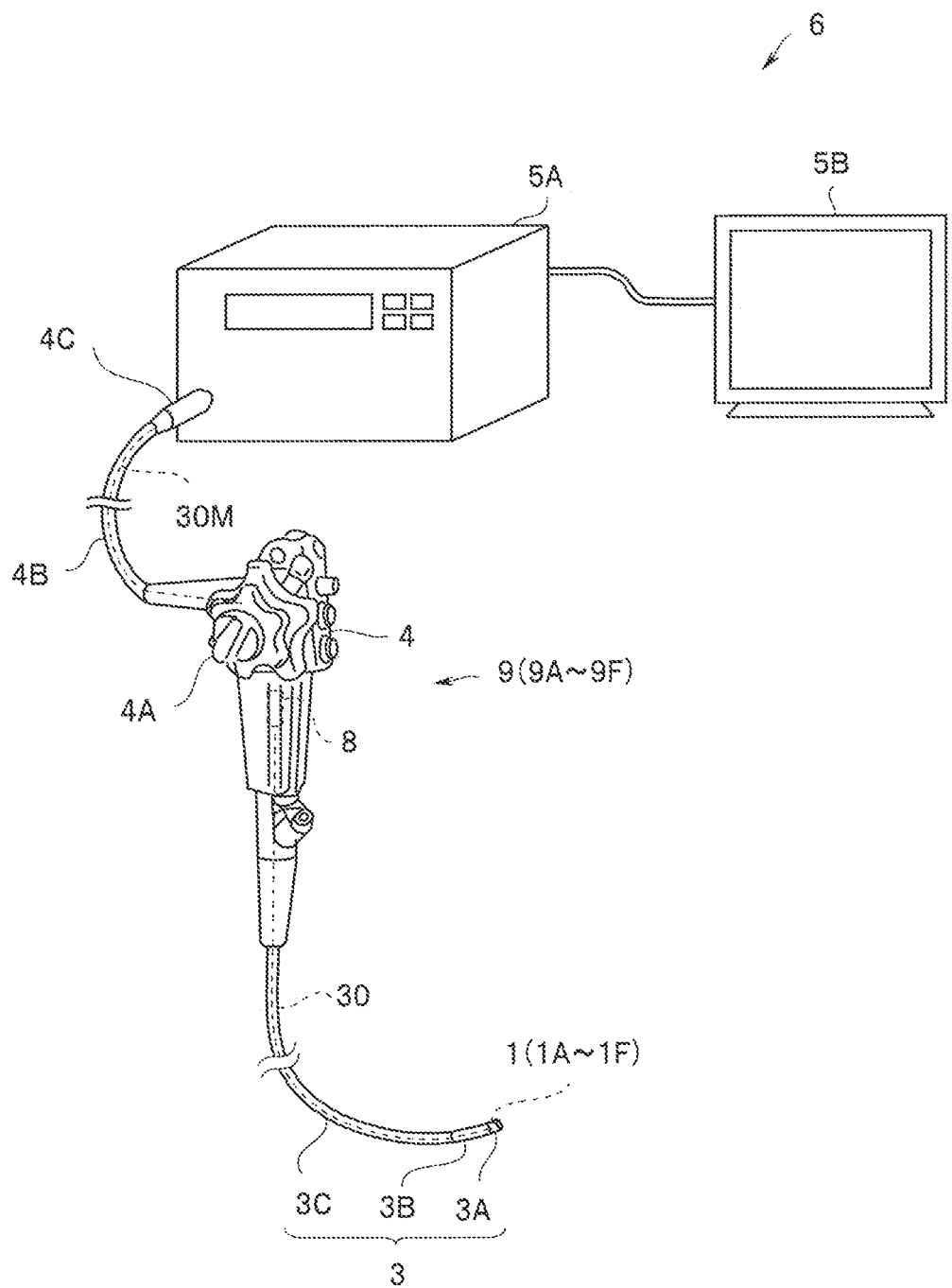
FIG. 1 is a configuration diagram of an endoscope system including an endoscope in an embodiment.

An endoscope 9, 9A to 9F in an embodiment shown in FIG. 1 configures an endoscope system 6 together with a processor 5A, a monitor 5B. An image pickup apparatus for endoscope 1, 1A to 1F (hereinafter referred to as an "image pickup apparatus") in the embodiment is disposed in the endoscope 9, 9A to 9F.

The endoscope 9 includes an insertion section 3, a grasping section 4 disposed at a proximal end portion of the insertion section 3, a universal cord 4B extended from the grasping section 4, and a connector 4C disposed at a proximal end portion of the universal cord 4B. The insertion section 3 includes a distal end portion 3A, a bending section 3B extended from the distal end portion 3A, bendable, and for changing a direction of the distal end portion 3A, and a flexible portion 3C extended from the bending section 3B. A turning angle knob 4A, which is an operation section for a surgeon to operate the bending section 3B, is disposed in the grasping section 4.

The universal cord 4B is connected to the processor 5A by the connector 4C. The processor 5A controls the entire endoscope system 6, performs signal processing on an image pickup signal, and outputs the image pickup signal as an image signal. The monitor 5B displays, as an endoscopic image, the image signal outputted by the processor 5A. Note that the endoscope 9 is a flexible endoscope but may be a rigid endoscope. The endoscope 9 may be for medical use or may be for industrial use.

The image pickup apparatus 1 small in size is disposed at the distal end portion 3A of the endoscope 9. The image pickup apparatus 1 includes an E/O type optical module including an optical element 20 (see FIG. 2 and the like) that converts an electric signal into an optical signal.

The optical signal is converted into an electric signal by an O/E type optical module 8 disposed in the grasping section 4 by passing through an optical fiber 30 inserted through the insertion section 3 and is transmitted by passing through an electric cable 30M inserted through the universal cord 4B. In other words, the image pickup signal is transmitted by passing through the optical fiber 30 in the insertion section 3 small in diameter and is transmitted by passing through the electric cable 30M larger in diameter than the optical fiber 30 in the universal cord 4B that is not inserted into a body and has less limitation of an outer diameter.

Note that when the optical module 8 is disposed in the connector 4C, the optical fiber 30 is inserted through the universal cord 4B.

The optical module 8 is disposed in the grasping section 4 having a relatively wide disposition space but may have the same configuration as a configuration of the optical module of the image pickup apparatus 1.

As explained below, the image pickup apparatus 1, 1A to 1F is small and easy to manufacture. Accordingly, the endoscope 9, 9A to 9F is minimally invasive and easy to manufacture.

First Embodiment

Figure 2:
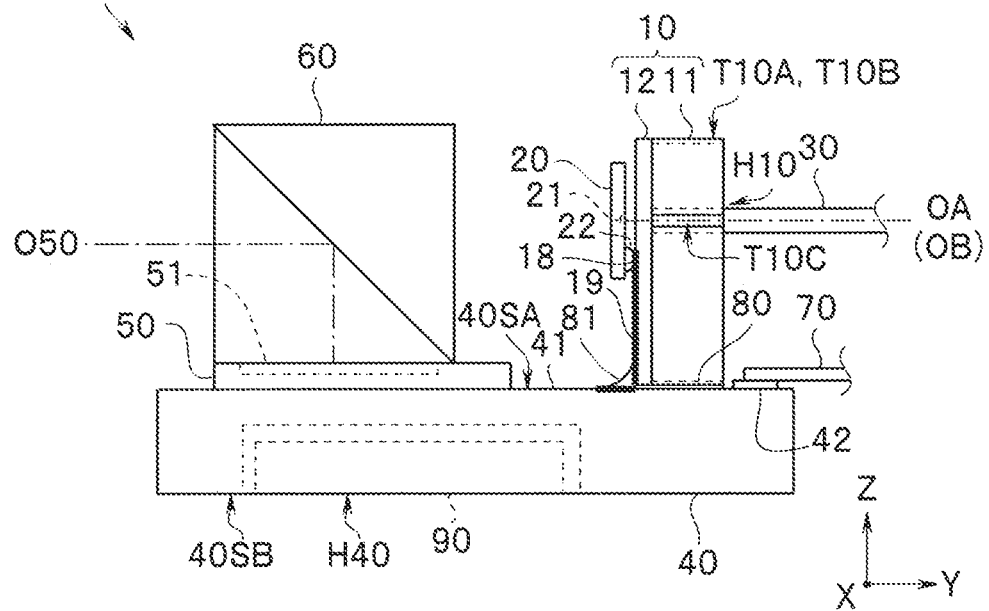
FIG. 2 is a side view of an image pickup apparatus in a first embodiment.
Figure 3:
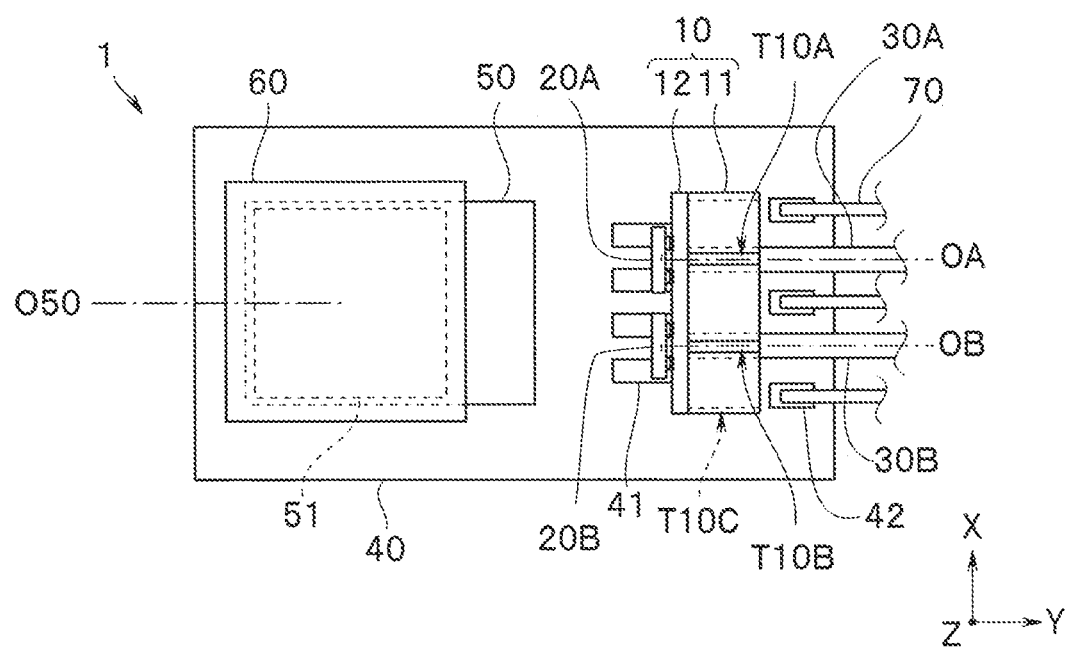
FIG. 3 is a top view of the image pickup apparatus in the first embodiment.
Figure 4:
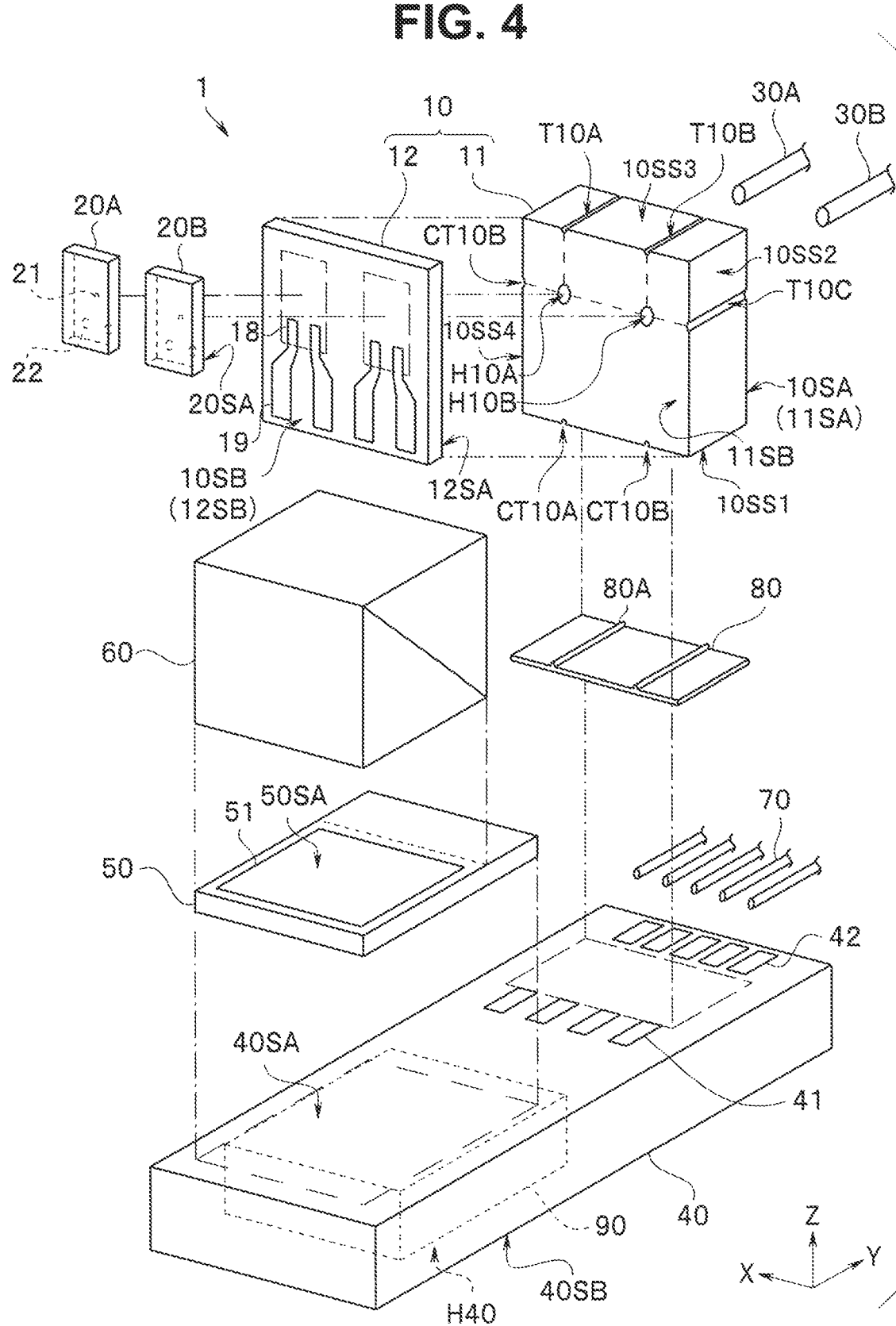
FIG. 4 is a perspective exploded view of the image pickup apparatus in the first embodiment.

The image pickup apparatus 1 in a first embodiment is explained with reference to FIG. 2 to FIG. 4. The image pickup apparatus 1 in the present embodiment converts an image pickup signal into an optical signal and transmits the optical signal.

In the following explanation, it should be noted that drawings based on each embodiment are schematic and relations between thicknesses and widths of each portion, ratios of the thicknesses of the respective portions, and the like are different from real ones. Portions, relations and ratios among dimensions of which are different, are sometimes included among the drawings. Illustration of and imparting of signs to a part of components are sometimes omitted. A direction of an object is referred to as "front".

The image pickup apparatus 1 includes, as main components, a ferrule 10, optical elements 20A, 20B, optical fibers 30A, 30B, and an image sensor 50. In other words, the image pickup apparatus 1 includes the optical elements 20A, 20B and the optical fibers 30A, 30B for respectively transmitting respective optical signals outputted by the optical elements 20A, 20B. Insertion holes H10A, H10B, into which the optical fibers 30A, 30B are respectively inserted, are present in the ferrule 10.

In the following explanation, when each of a plurality of components is referred to, one character at an end of a sign is omitted. For example, each of the optical elements 20A, 20B is referred to as an optical element 20.

The image sensor 50 is a CCD chip or a CMOS image pickup chip, on a light receiving surface 50SA of which a prism 60 is disposed. The image sensor 50 is disposed on a mounting surface 40SA of a wiring board 40 including the mounting surface 40SA and a back surface 40SB on the reverse side of the mounting surface 40SA. An image pickup signal outputted by a light receiving unit 51 of the light receiving surface 50SA is converted into, by a drive element 90, a driving signal for causing the optical element 20 to emit light.

The ferrule 10 includes a ferrule body 11 and a front plate 12. The ferrule body 11 is made of, for example, silicon, glass, or resin. The front plate 12 is made of a transparent material, for example, glass. The ferrule 10 including the ferrule body 11 made of silicon and the front plate 12 made of glass is explained as an example below.

The ferrule body 11 includes a first principal surface 11SA and a second principal surface 11SB on the reverse side of the first principal surface 11SA. The front plate 12 includes a third principal surface 12SA and a fourth principal surface 12SB on the reverse side of the third principal surface 12SA.

The second principal surface 11SB of the ferrule body 11 is in contact with the third principal surface 12SA of the front plate 12.

The ferrule 10 is a rectangular parallelepiped including a rear surface 10SA, which is the first principal surface 11SA of the ferrule body 11, a front surface 10SB, which is the fourth principal surface 12SB of the front plate 12, and four side surfaces 10SS (10SS1, 10SS2, 10SS3, 10SS4).

Insertion holes H10 piercing through the first principal surface 11SA to the second principal surface 11SB are present in the ferrule body 11. Bottom surfaces of the insertion holes H10 are the third principal surface 12SA of the front plate 12.

Four sets of first electrodes 18 and second electrodes 19 connected to the first electrodes 18 are disposed on the fourth principal surface 12SB of the front plate 12 (the front surface 10SB of the ferrule 10). The four sets of the electrodes are respectively electrically connected to external electrodes of the two optical elements 20A, 20B.

The optical element 20 is a surface emitting laser or the like including, on a light emitting surface 20SA, a light emitting region 21 that outputs light of an optical signal. For example, the optical element 20 ultrasmall in size having a plan view dimension as small as 250 µm×250 µm includes, on the light emitting surface 20SA, the light emitting region 21 having a diameter of 10 m and an external electrode 22 that supplies a driving signal to the light emitting region 21.

The optical elements 20A, 20B are disposed on the fourth principal surface 12SB of the front plate 12 in a state in which the light emitting regions 21 of the optical elements 20A, 20B are opposed to the insertion holes H10A, H10B of the ferrule body 11.

The optical fibers 30A, 30B for transmitting an optical signal are inserted into the insertion holes H10A, H10B of the ferrule body 11.

The wiring board 40 includes, as a base, FPC, ceramic, glass epoxy, glass, silicon, or the like. The drive element 90 is housed in a recess H40 of the back surface 40SB. A first side surface 10SS1 of the ferrule 10 is bonded to the mounting surface 40SA by an adhesive 80. The second electrodes 19 on the front surface 10SB of the ferrule 10 (the fourth principal surface 12SB of the front plate 12) are electrically connected to third electrodes 41 on the mounting surface 40SA. For the connection, a conductive bonding member 81 such as solder or a conductive adhesive is used. The driving signal based on the image pickup signal outputted by the drive element 90 is inputted to the external electrode 22 bonded to the first electrodes 18 by passing through the third electrodes 41 and the second electrodes 19.

Cables 70 for transmitting an electric signal are electrically connected to fourth electrodes 42 on the mounting surface 40SA using a conductive bonding member. The electric signal is, for example, a power signal or a control signal of the image sensor 50.

In the ferrule 10 of the image pickup apparatus 1, trenches T10A, T10B are present on a third side surface 10SS3 parallel to the first side surface 10SS1 bonded to the mounting surface 40SA. Further, a trench T10C is present on a second side surface 10SS2 orthogonal to the third side surface 10SS3. An extending direction of the trenches T10A (T10B), T10C is parallel to a depth direction of the insertion holes H10. Length of the trenches T10A (T10B), T10C is the same as depth of the insertion holes H10. In other words, trenches T10 are formed on the side surfaces of the ferrule body 11 and are not formed on the side surfaces of the front plate 12.

The respective trenches T10A, T10B, T10C formed on two orthogonal side surfaces 10SS (the third side surface 10SS3, the second side surface 10SS2) among the four side surfaces 10SS are insertion supporting trenches corresponding to positions where the insertion holes H10 are projected onto the respective side surfaces 10SS. For example, a center line of the insertion holes H10A, H10B projected onto the third side surface 10SS3 and a center line of the trenches T10A, T10B coincide.

In the ferrule 10, positions of the insertion holes H10 cannot be confirmed from the side surfaces 10SS. Accordingly, it is not easy to insert the optical fibers 30 into the insertion holes H10 of the ferrule 10. However, as explained below, the positions of the insertion holes H10 can be confirmed from the side surfaces 10SS because the insertion supporting trenches T10 on the side surfaces 10SS of the ferrule 10 are present. Therefore, it is easy to manufacture the image pickup apparatus 1.

Note that, on a side surface parallel to a side surface on which the trenches T10 are formed, counter trenches CT10 are formed on same positions as the trenches T10. For example, on the first side surface 10SS1 parallel to the third side surface 10SS3 on which the trench T10A is formed, a counter trench CT10A is formed in a relative position in the first side surface 10SS1 same as a relative position of the trench T10A in the third side surface 10SS3.

Counter trenches CT10A, CT10B formed on the first side surface 10SS1 are buffer trenches. The adhesive 80 is disposed in the counter trenches CT10A, CT10B. The adhesive 80 disposed in the counter trenches CT10A, CT10B stores an excessive adhesive and has an adhesive intensity improvement effect.

<Manufacturing Method for the Image Pickup Apparatus>

Figure 5:
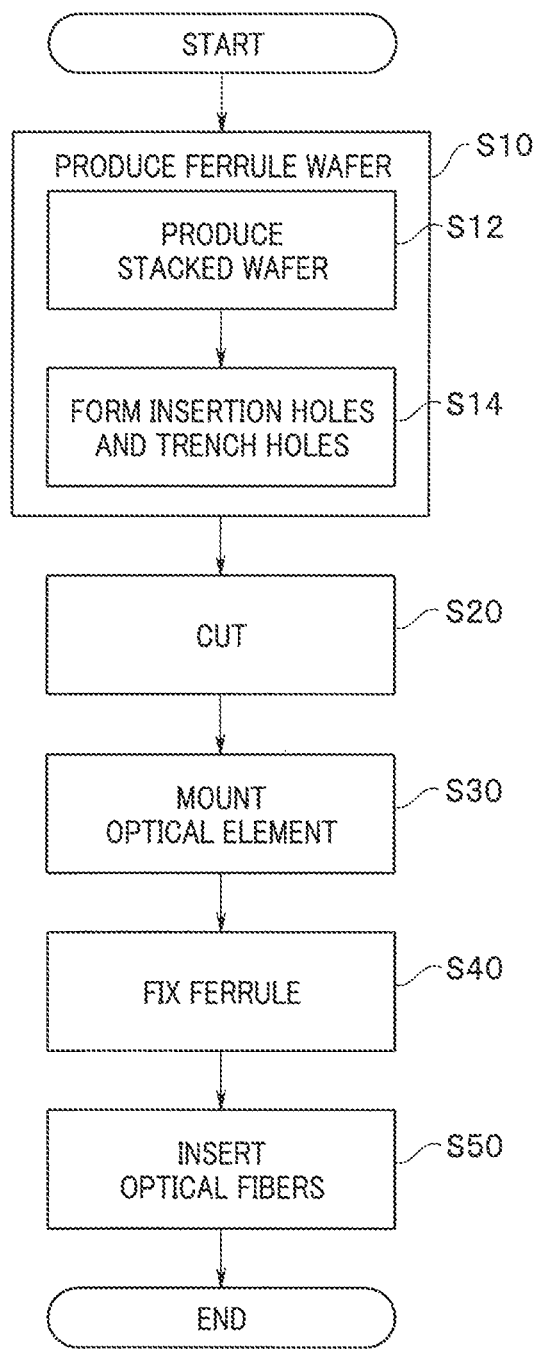
FIG. 5 is a flowchart of a manufacturing method for the image pickup apparatus in the first embodiment.

A manufacturing method for the image pickup apparatus 1 is explained with reference to a flowchart of FIG. 5.

<Step S10> Ferrule Wafer Producing Step

A ferrule wafer producing step S10 includes a stacked wafer producing step S12 and an insertion hole and trench hole forming step S14.

<Step S12> Stacked Wafer Producing Step

Figure 6:
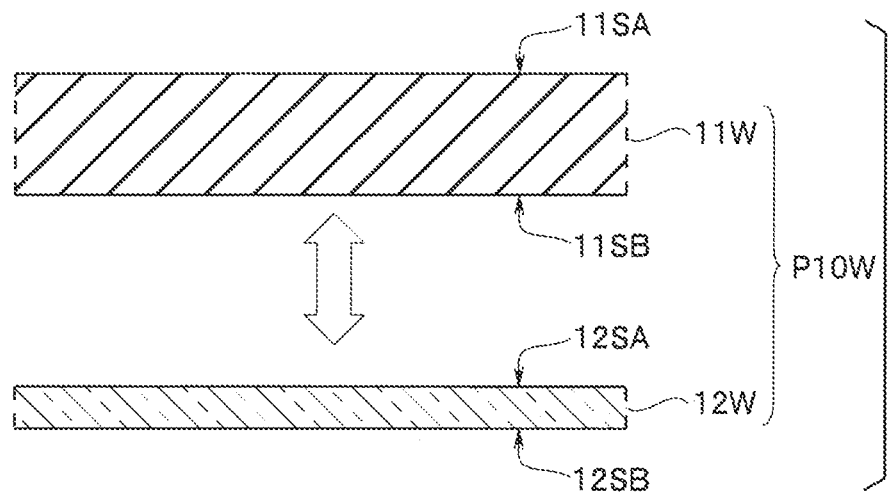
FIG. 6 is a sectional view for explaining the manufacturing method for the image pickup apparatus in the first embodiment.

As shown in FIG. 6, a silicon wafer 11W including the first principal surface 11SA and the second principal surface 11SB and a glass wafer 12W including the third principal surface 12SA and the fourth principal surface 12SB are bonded and a stacked wafer P10W is produced.

For example, the second principal surface 11SB of the silicon wafer 11W and the third principal surface 12SA of the glass wafer 12W are integrated by bonding such as anodic bonding or low-temperature bonding or an adhesive in a state in which the second principal surface 11SB and the third principal surface 12SA are in contact.

On the fourth principal surface 12SB of the glass wafer 12W, the first electrodes 18 to which the optical element 20 is bonded and the second electrodes 19 are disposed.

<Step S14> Etching Step

Figure 7:
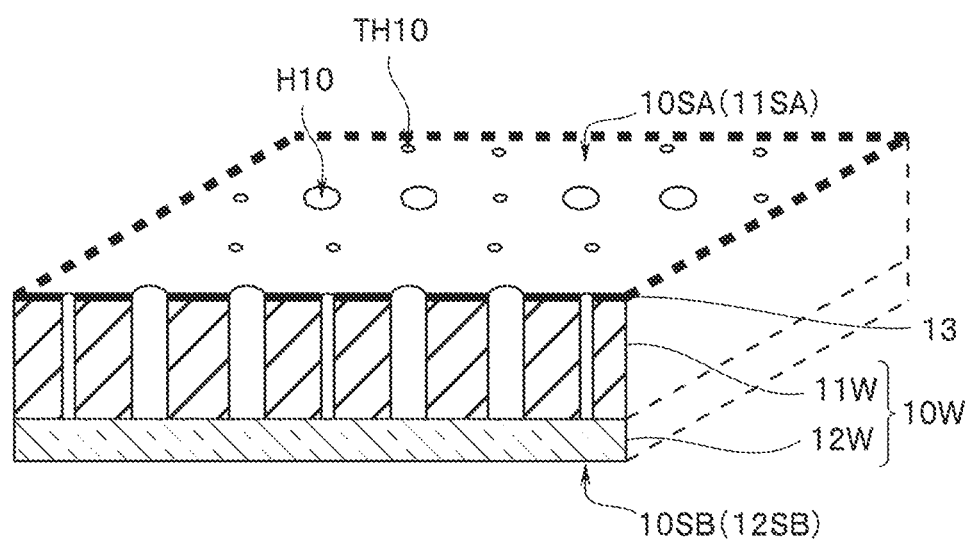
FIG. 7 is a sectional perspective view for explaining the manufacturing method for the image pickup apparatus in the first embodiment.

As shown in FIG. 7, the stacked wafer P10W is etched to be a ferrule wafer 10W. In other words, on the first principal surface 11SA of the stacked wafer P10W, for example, an etching mask 13 made of silicon oxide is disposed. A plurality of insertion holes H10 and a plurality of trench holes TH10 are simultaneously formed by etching by a DEEP-RIE method. As explained below, "trench hole" is a hole that becomes a trench in a cut surface when a wafer is cut.

In the etching by the RIE (reactive ion etching) method, for example, a hole having a high aspect ratio is formed by repeating etching by $SF_4$ gas and protective film formation on a wall surface. Since glass (silicon oxide) is hardly etched, the insertion holes H10 and the trench holes TH10 have the glass wafer 12W as bottom surfaces. In other words, depth of the insertion holes H10 and the trench holes TH10 is the same as thickness of the silicon wafer 11W. An inner diameter of the insertion holes H10 is substantially the same as an outer diameter of the optical fibers 30 inserted into the insertion holes H10.

Openings for insertion hole formation and openings for trench hole formation of the etching mask are formed in extremely accurate relative positions by a photolithography method.

Note that the openings of the etching mask are not limited to a circle but may be an ellipse, a quadrangle, a hexagon, or the like.

<Step S20> Cutting Step

Figure 8:
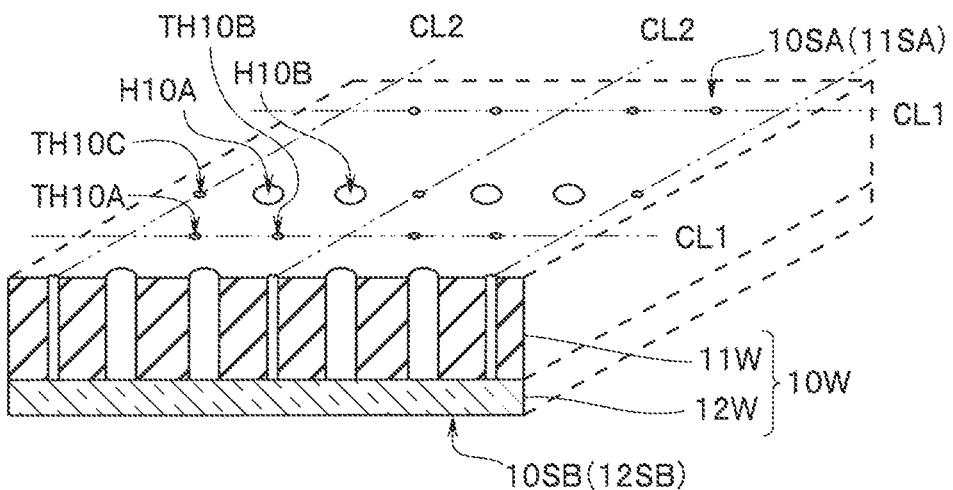
FIG. 8 is a sectional perspective view for explaining the manufacturing method for the image pickup apparatus in the first embodiment.
Figure 9:
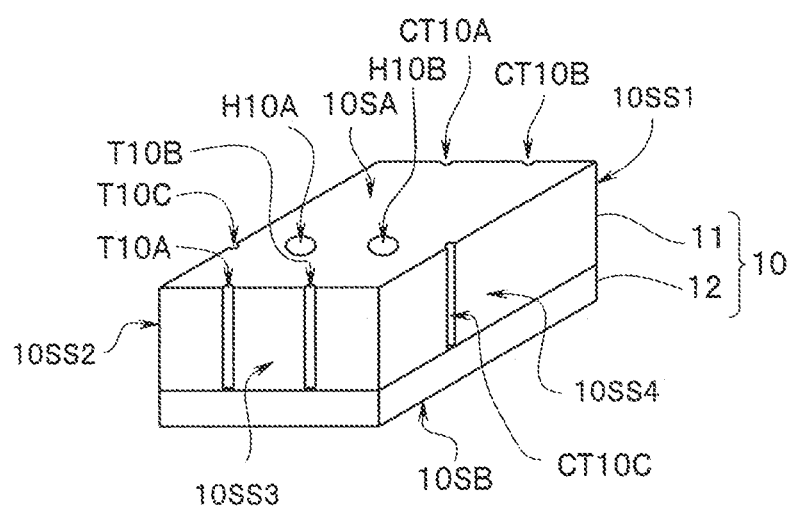
FIG. 9 is a perspective view of a ferrule of the image pickup apparatus in the first embodiment.

As shown in FIG. 8, the rectangular parallelepiped ferrule 10 shown in FIG. 9 is produced by cutting the ferrule wafer 10W along the orthogonal cutting lines CL1, CL2 extending across the trench holes TH10 (TH10A, TH10B, TH10C).

The ferrule 10 includes the rear surface 10SA, the front surface 10SB, and the four side surfaces 10SS. In the ferrule body 11 made of silicon, the insertion holes H10, the trenches T10, and the counter trenches CT10 are formed. When the ferrule wafer 10W is cut along the cutting lines CL extending across the trench holes TH10, one trench hole TH10 changes to the trench T10 of the ferrule 10 and the counter trench CT10 of a ferrule different from the ferrule 10. In other words, cut surfaces of the trench holes TH10 of the trenches T10 are formed as opening surfaces.

In other words, inner surfaces of the trenches T10 and the counter trenches CT10 are wall surfaces of the trench holes TH10 formed simultaneously with the insertion holes H10. However, in a structure in which the trench holes TH10 are formed simultaneously with the insertion holes H10, a word for specifying a structure in which the trench holes TH10 and the insertion holes H10 are separately formed and a structure relating to a difference between the trench holes TH10 and the insertion holes H10 cannot be found. Further, appropriate means for analyzing the structures is absent. Therefore, it is also impossible to analyze and specify such structures.

The insertion holes H10 and the trench holes TH10 are simultaneously formed and share the glass wafer 12W as the bottom surfaces. Accordingly, an extending direction of the trenches T10 and the counter trenches CT10 is parallel to the depth direction of the insertion holes H10. Length of the trenches T10 and the counter trenches CT10 is the same as thickness of the silicon wafer 11W, which is the depth of the insertion holes H10.

Note that the ferrule 10, which is a quadrangular prism, may be machined into an octagonal prism by chamfering sides of the ferrule 10. The sides of the ferrule 10 may be chamfered in a curved line shape. In other words, the ferrule 10 may be a substantial parallelepiped.

<Step S30> Optical Element Mounting Step

The optical element 20 is mounted in a position where the light emitting region 21 of the optical element 20 is opposed to the insertion holes H10 on the front surface 10SB of the ferrule 10. In other words, the external electrode 22 of the optical element 20 is bonded to the first electrodes 18 on the front surface 10SB.

<Step S40> Ferrule Fixing Step

The ferrule 10, on which the optical element 20 is mounted, is bonded to the mounting surface 40SA of the wiring board 40 using the adhesive 80. The second electrodes 19 of the ferrule 10 are electrically connected to the third electrodes 41 of the wiring board 40 using the conductive bonding member 81 such as solder or a conductive adhesive.

<Step S50> Optical Fiber Inserting Step

Figure 10:
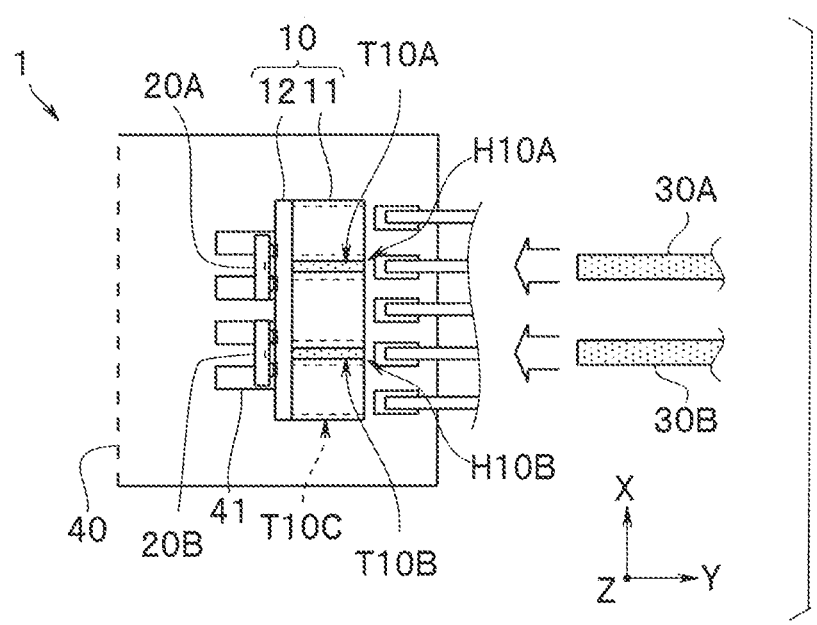
FIG. 10 is a top view of a main part for explaining the manufacturing method for the image pickup apparatus in the first embodiment.

As shown in FIG. 10, the optical fibers 30 are inserted into the insertion holes H10 of the ferrule 10.

For example, the optical fibers 30 are formed by 50 μm-diameter cores for transmitting light and 125 μm-diameter clads covering outer circumferences of the cores. It is not easy to insert the optical fibers 30 having an outer diameter of 125 μm into the insertion holes H10 having an inner dimeter of 130 μm. However, in the ferrule 10, the trenches T10, which are the insertion supporting trenches, are formed in the positions where the insertion holes H10 are projected onto the side surface 10SS.

For example, the optical fiber 30A is fixed to a jig movable in X, Y, and Z directions, positioned in the X direction based on the trench T10A, and positioned in the Z direction based on the trench T10C. Since the positions of the insertion holes H10 can be confirmed from the side surface 10SS, in the ferrule 10, the optical fibers 30 can be easily inserted into the insertion holes H10.

Image pickup apparatuses for endoscope 1A to 1F in embodiments or modifications explained below are similar to the image pickup apparatus 1 and have the same effects. Therefore, components having the same functions are denoted by the same reference numerals and signs and explanation of the components is omitted.

<Modification of the First Embodiment>

Figure 11:
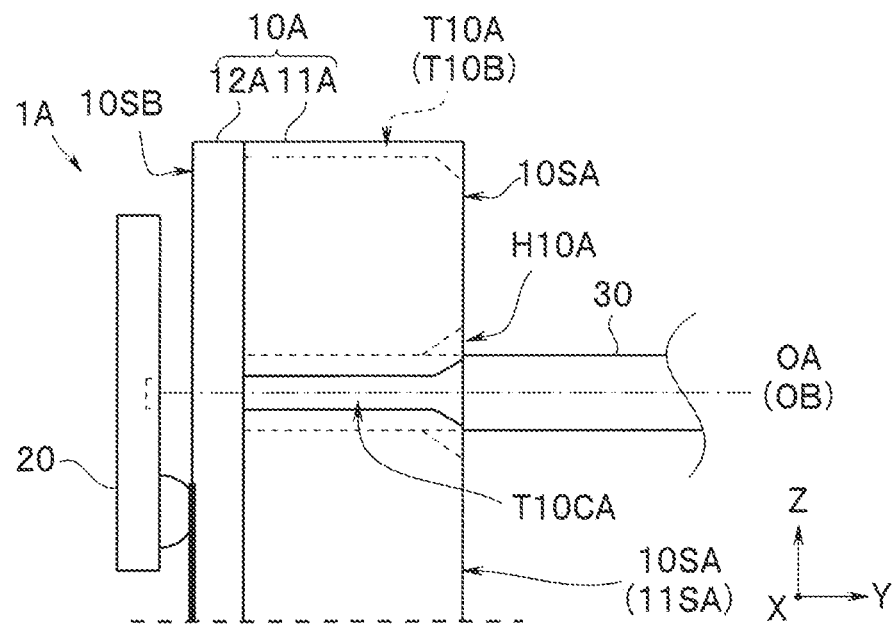
FIG. 11 is a side view of a main part of an image pickup apparatus in a modification 1 of the first embodiment.

As shown in FIG. 11, in the image pickup apparatus 1A in the modification, a hole opening on the rear surface 10SA of the insertion hole H10 and a trench opening on the rear surface 10SA of the trench T10 of a ferrule 10A are respectively tapered.

Since the hole opening of the insertion hole H10 is tapered, in the image pickup apparatus 1A, the optical fibers 30 are more easily inserted into the insertion holes H10 than in the image pickup apparatus 1.

In a manufacturing method for the ferrule 10A, the ferrule wafer producing step S10 (the etching step S14) includes a silicon anisotropic etching step and a DEEP-RIE step.

Figure 12:
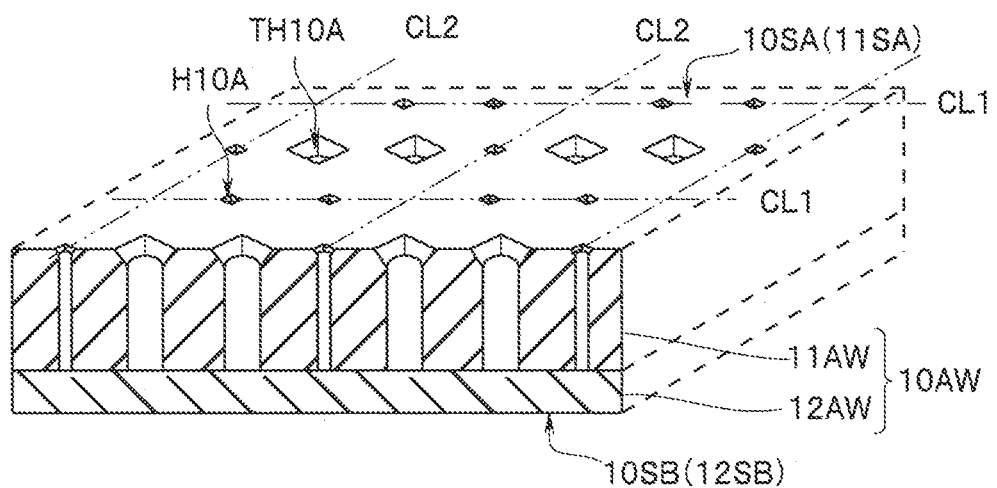
FIG. 12 is a sectional perspective view for explaining a manufacturing method for an image pickup apparatus in a modification 2 of the first embodiment.

As shown in FIG. 12, in a ferrule wafer 10AW, the insertion holes H10 and the trench holes TH10 on the first principal surface 10SA (11SA) are tapered.

First, tapers are formed in the silicon anisotropic etching step and, thereafter, the insertion holes H10 having a second wiring board wafer 12AW as bottom surfaces are formed by the DEEP-RIE step. In the DEEP-RIE step, the second wiring board wafer 12AW has an etching stop function.

In anisotropic etching, in a silicon wafer 11W in which the first principal surface 11SA is a silicon (100) surface, etching speed of a (111) surface in the etching step is slower compared with a (100) surface. Accordingly, a wall surface of an opening is formed as the (111) surface, an angle θ between the (111) surface and the (100) surface is 54.74 degrees, and a taper is formed. The taper of the insertion holes H10 and the taper of the trench holes TH10 have the same angle with respect to the first principal surface 11SA.

As anisotropic etching, a wet etching method using a tetramethylammonium hydroxide (TMAH) water solution, a potassium hydroxide (KOH) water solution, or the like is desirable.

The silicon anisotropic etching method is used in the method explained above. However, a silicon isotropic dry etching method such as reactive ion etching (RIE) or chemical dry etching (CDE) can also be used. In this case, after an insertion hole is formed in the DEEP-RIE step, a taper is formed using silicon isotropic dry etching.

Second Embodiment

Figure 13:
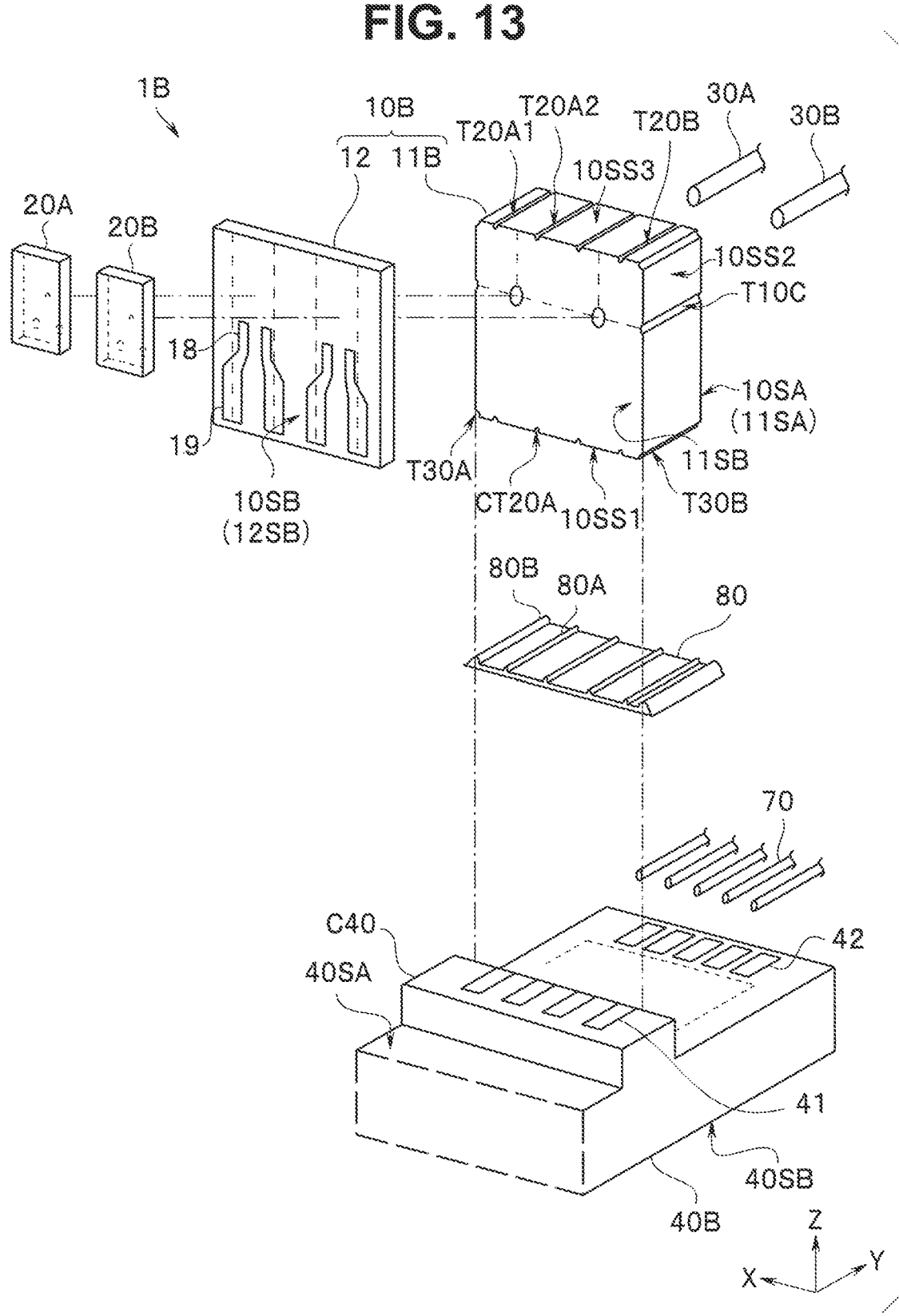
FIG. 13 is a perspective exploded view of a main part of an image pickup apparatus in a second embodiment.

As shown in FIG. 13, in the image pickup apparatus 1B in a second embodiment, cutout trenches T30 (T30A, T30B) are formed in end sides of the first side surface 10SS1 bonded to the mounting surface 40SA of a wiring board 40B among the four side surfaces 10SS of a ferrule 10B. The adhesive 80 (80B) is disposed in the cutout trenches T30.

Four trenches T20 (T20B1*i*, T20B2, T20C) on the third side surface 10SS3 of the ferrule 10B are alignment trenches respectively formed in positions corresponding to positions of the respective four second electrodes 19 on the front surface 10SB.

<Manufacturing Method for the Image Pickup Apparatus 1B>

Figure 14:
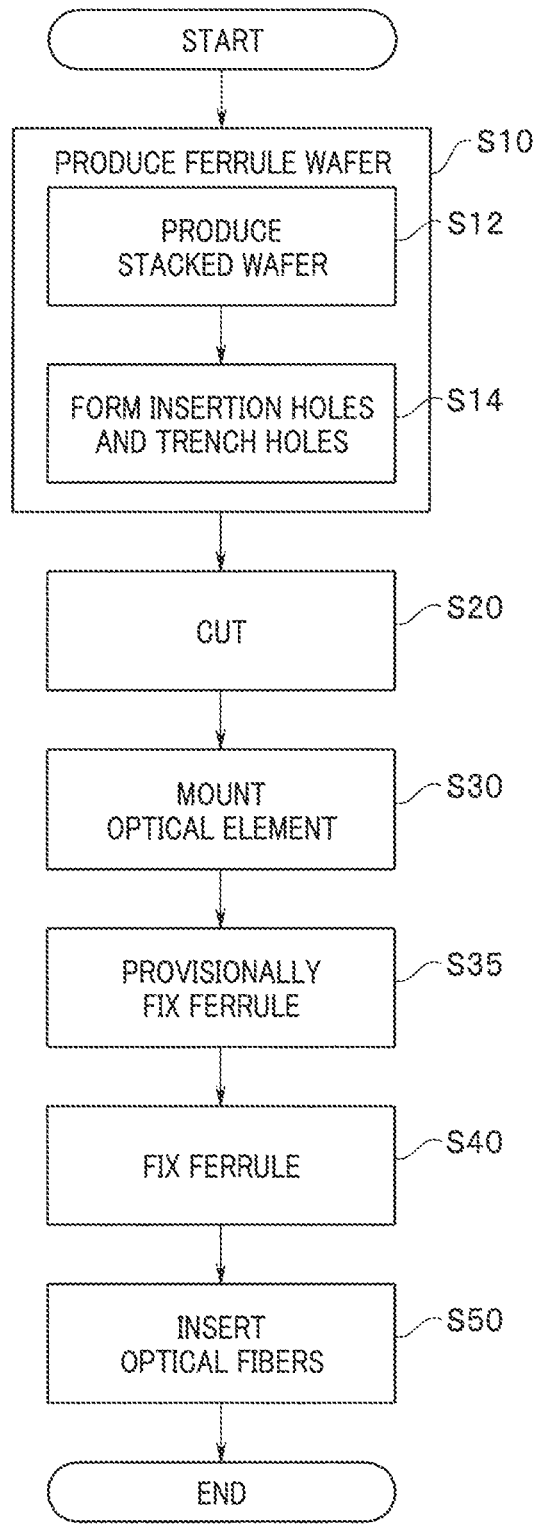
FIG. 14 is a flowchart of a manufacturing method for the image pickup apparatus in the second embodiment.

A manufacturing method for the image pickup apparatus 1B is explained with reference to a flowchart of FIG. 14. Note that the same explanation as the explanation of the flowchart of FIG. 5 is omitted.

<Step S14> Etching Step

A ferrule wafer in which a trench hole is present in a crossing part of the cutting lines CL1, CL2 is produced.

<Step S20> Cutting Step

The ferrule wafer is cut and the ferrule 10B is produced. The cutting lines CL1, CL2 cross each other at the trench hole. In other words, one trench hole changes to the cutout trenches T30 of four ferrules having cut surfaces of the trench hole as opening surfaces. In the ferrule 10B, the cutout trenches T30 (T30A, T30B) are formed in end sides of the first side surface 10SS1 (and the third side surface 10SS3).

The trenches T20 (T20A, T20B) on the third side surface 10SS3 of the ferrule 10B are alignment trenches formed in positions corresponding to positions of the second electrodes 19 on the front surface 10SB. The positions of the second electrodes 19 correspond to the positions of the insertion holes H10. For example, when the insertion holes H10 are projected onto the third side surface 10SS3, the insertion holes H10 are intermediate lines of the two trenches T20B1, T20B2. In other words, the trenches T20 are the alignment trenches and, at the same time, insertion supporting trenches.

<Step S35> Ferrule Provisional Fixing Step

The ferrule 10B is provisionally fixed to the mounting surface 40SA of the wiring board 40B.

In the wiring board 40B, a protrusion C40 is present on the mounting surface 40SA. The third electrodes 41 are disposed on an upper surface of the protrusion C40. The front surface 10SB is brought into contact with a wall surface of the protrusion C40, whereby the ferrule 10B is automatically positioned in a Y-axis direction. The ferrule 10B is positioned in the X direction, that is, the second electrodes 19 and the third electrodes 41 are positioned using the trenches T20, which are the alignment trenches.

The ferrule 10B and the wiring board 40B are positioned by the protrusion C40 and the trenches T20.

In a state in which the ferrule 10B and the wiring board 40B are positioned, the ferrule 10B is provisionally fixed to the wiring board 40B, for example, using a small amount of the adhesive 80 for the purpose of not moving the ferrule 10B.

<Step S40> Ferrule Fixing Step

The adhesive 80, which is unhardened and is liquid, is injected into the cutout trenches T30A on the first side surface 10SS1 of the ferrule 10B. The adhesive 80 intrudes into a gap between the first side surface 10SS1 and the mounting surface 40SA with interfacial tension. The ferrule 10B is firmly fixed to the wiring board 40B by hardening of the adhesive 80.

The second electrodes 19 on the front surface 10SB of the ferrule 10B and the third electrodes 41 on the wiring board 40B are bonded by, for example, solder.

Note that when the ferrule and the wiring board are fixed, if the adhesive 80 disposed on a bonding surface is excessive, the adhesive 80 overflows the bonding surface. If the adhesive 80 covers the second electrodes 19 on the front surface 10SB of the ferrule, it is likely that a bonding failure of the second electrodes 19 and the third electrodes 41 occurs. In the image pickup apparatus 1B, the adhesive 80 is disposed in the cutout trenches T30 and intrudes into a gap of the bonding surface with interfacial tension. Accordingly, in the image pickup apparatus 1B, since the adhesive 80 is not excessively supplied to the bonding surface, a bonding failure does not occur.

<Step S50> Optical Fiber Inserting Step

The optical fibers 30 and the insertion holes H10 are positioned using the trenches T10A on the second side surface 10SS2 and the trenches T20 on the third side surface 10SS3. The optical fibers 30 are inserted into the insertion holes H10.

Third Embodiment

Figure 15:
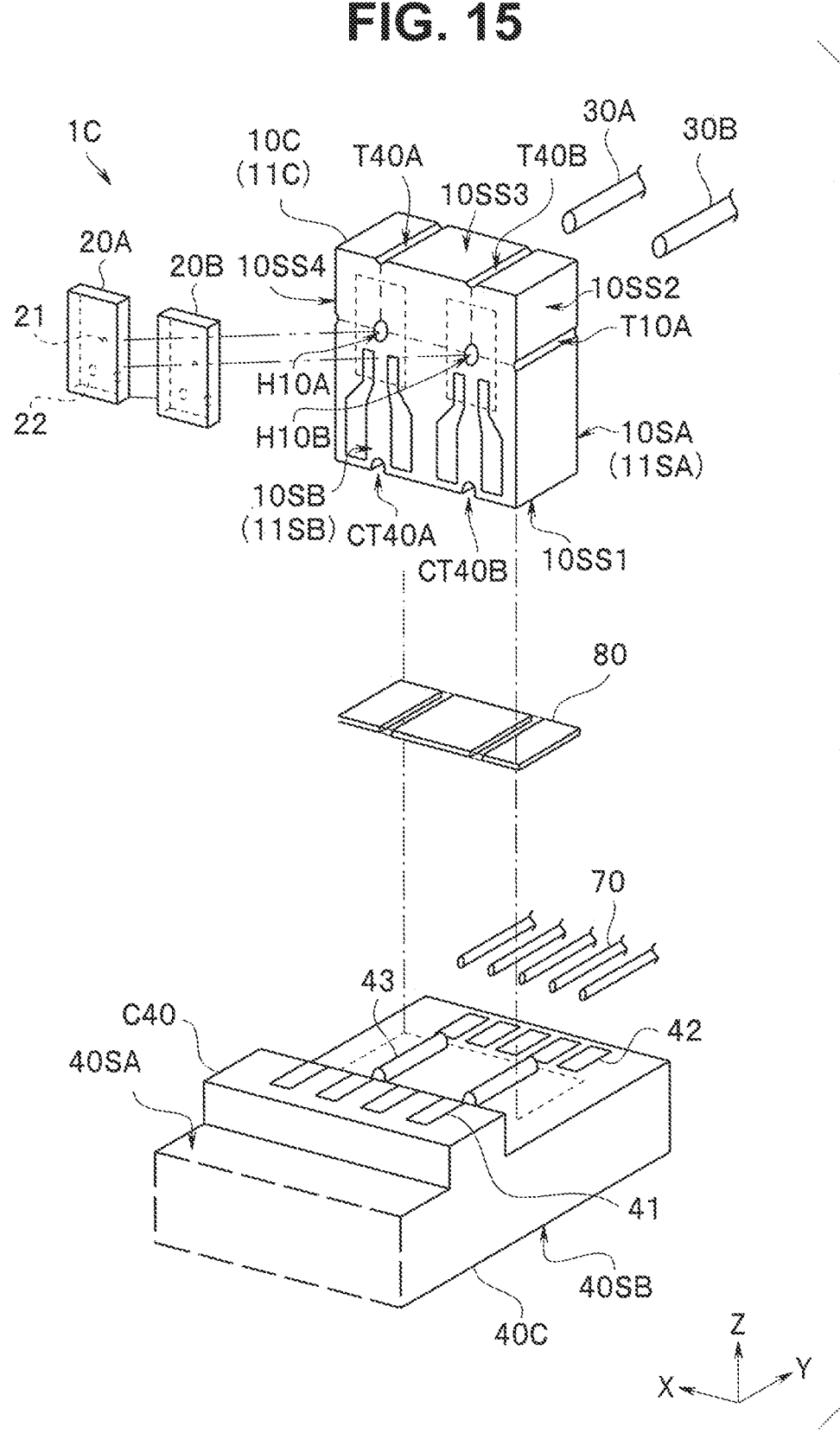
FIG. 15 is a perspective exploded view of a main part of an image pickup apparatus in a third embodiment.

As shown in FIG. 15, a ferrule 10C of the image pickup apparatus 1C does not include a front plate. A ferrule body 11C made of silicon, glass, resin, or the like is the ferrule 10C. On the front surface 10SB of the ferrule 10C, the first electrodes 18 and the second electrodes 19 connected to the first electrodes 18 are disposed.

In other words, the ferrule of the present invention may not include a transparent or nontransparent front plate.

In the ferrule 10C, insertion holes and trench holes are formed after a silicon wafer is bonded to a support wafer.

Figure 16:
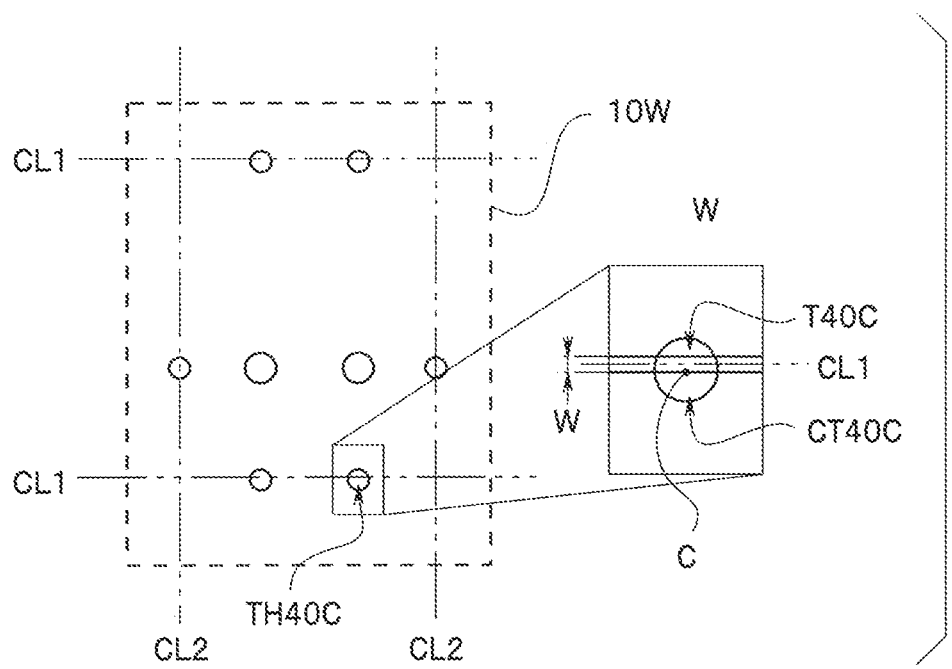
FIG. 16 is a top view for explaining a manufacturing method for the image pickup apparatus in the third embodiment.

As shown in FIG. 16, for example, the cutting line CL1 for cutting a silicon wafer, in which holes are formed, extends across a trench hole TH40C but is slightly separated from a center C of the trench hole TH40C. Margin width W lost by the cutting is smaller than a radius of the trench hole TH40C.

Accordingly, an insertion supporting trench T40C and a counter trench CT40C are formed by the cutting but the insertion supporting trench T40C and the counter trench CT40C have different widths and depths. Although the ferrule 10C is ultrasmall in size, it is easy to distinguish the first side surface 10SS1 and the third side surface 10SS3.

On the other hand, on the mounting surface 40SA of a wiring board 40C, projections 43 fit with the counter trench CT40C are disposed. The projections 43 are elongated ridges made of resin or metal. A plurality of columnar bumps can also be used as the projections 43.

For the purpose of fitting the ridges 43 with a counter trench CT40, by disposing the ferrule 10C on the mounting surface 40SA, the ferrule 10C is positioned in the X direction, that is, the second electrodes 19 and the third electrodes 41 are positioned. In other words, the counter trench CT40 is a positioning trench.

Since the counter trench CT40 is wider and deeper than an insertion supporting trench T40, the projections 43 easily fit with the counter trench CT40.

Fourth Embodiment

Figure 17:
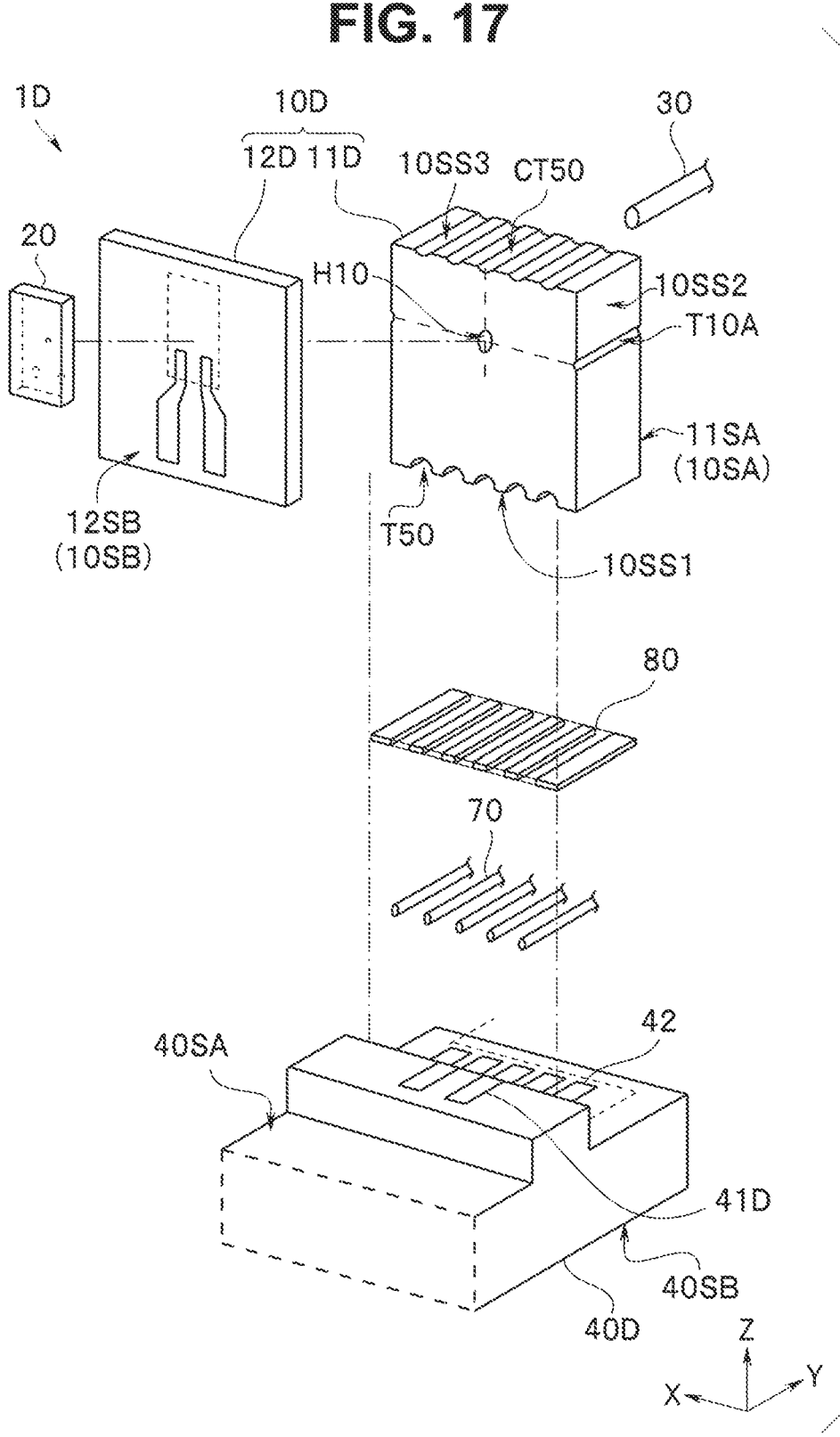
FIG. 17 is a perspective exploded view of a main part of an image pickup apparatus in a fourth embodiment.

As shown in FIG. 17, the image pickup apparatus 1D in the present embodiment includes only one optical element 20 and one optical fiber 30. Only one optical element 20 is mounted on the fourth principal surface 12SB of a front plate 12D (the front surface 10SB of a ferrule 10D). One insertion hole H10 is formed in a ferrule body 11D.

In the image pickup apparatus 1D, trenches formed on the first side surface 10SS1 of the ferrule 10D (the ferrule body 11D) are connection trenches T50 into which cables 70 are inserted.

The fourth electrodes 42 on a wiring board 40D are disposed in positions opposed to the connection trenches T50. In other words, connection holes, on inner surfaces of which the fourth electrodes 42 are present, are formed by the mounting surface 40SA and the connection trenches T50. The cables 70 inserted into the connection trenches T50 are bonded to the fourth electrodes 42.

Since bonding parts (the fourth electrodes 42) of the cables 70 are housed in the connection trenches T50 of the ferrule 10D, the image pickup apparatus 1D is shorter and smaller than the image pickup apparatus 1.

Note that one of counter trenches on the third side surface 10SS3 of the ferrule 10D is an insertion supporting trench CT50 at a position corresponding to a position of the insertion hole H10.

Fifth Embodiment

Figure 18:
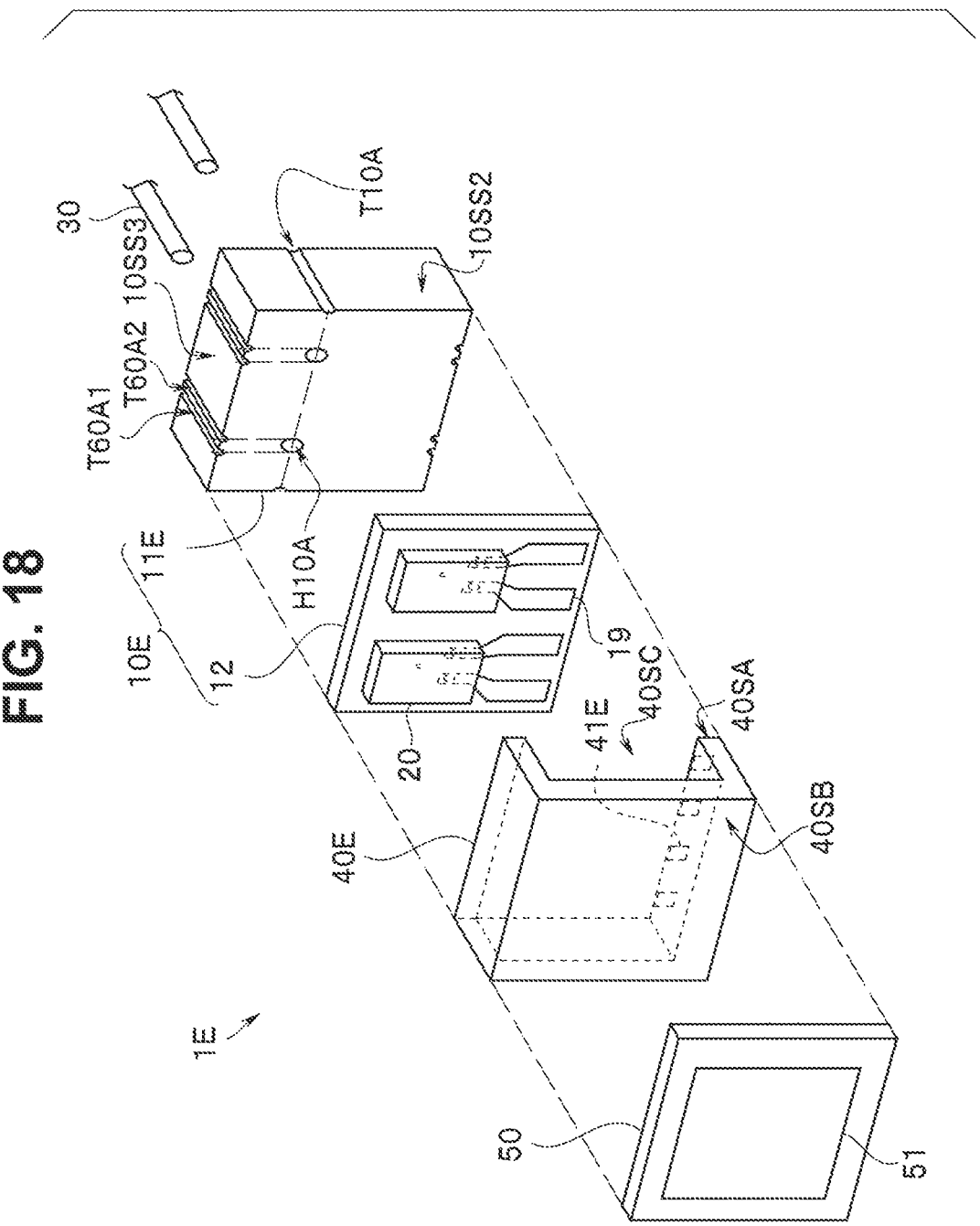
FIG. 18 is a perspective exploded view of an image pickup apparatus in a fifth embodiment.

As shown in FIG. 18, the image pickup apparatus 1E in the present embodiment is a vertical type. In a vertical-type image pickup apparatus, the image sensor 50 mounted on the back surface 40SB of a wiring board 40E is disposed in a vertical direction with respect to a major axis direction of the insertion section 3 of the endoscope. In contrast, the image pickup apparatus 1 shown in FIG. 4 or the like is a horizontal type in which the image sensor 50 is disposed in a horizontal direction with respect to the major axis direction of the insertion section 3.

The wiring board 40E is a solid wiring board including a flat plate section and a frame section. In the wiring board 40E, a third electrode 41E is disposed on the mounting surface 40SA in the frame section. The mounting surface 40SA comes into contact with the front surface 10SB of a ferrule 10E, whereby the second electrodes 19 of the ferrule 10E and third electrode 41E are connected. The optical element 20 is housed in a space 40SC formed by the frame section of the wiring board 40E. Although not shown, a cable may be bonded to the wiring board 40E.

Insertion supporting trenches T60 at a position corresponding to outer edges of the insertion holes H10 are formed on the third side surface 10SS3 of the ferrule 10E. For example, two trenches T60A1, T60A2 are formed on the third side surface 10SS3 to correspond to the insertion holes H10A. On the other hand, on the second side surface 10SS2, one insertion supporting trench T10 corresponding to a position of the insertion holes H10 is formed.

The image pickup apparatus 1E is a vertical type. However, like the horizontal-type image pickup apparatus 1 and the like, it is easy to insert the optical fibers 30 into the insertion holes H10.

<Modification of the Fifth Embodiment>

Figure 19:
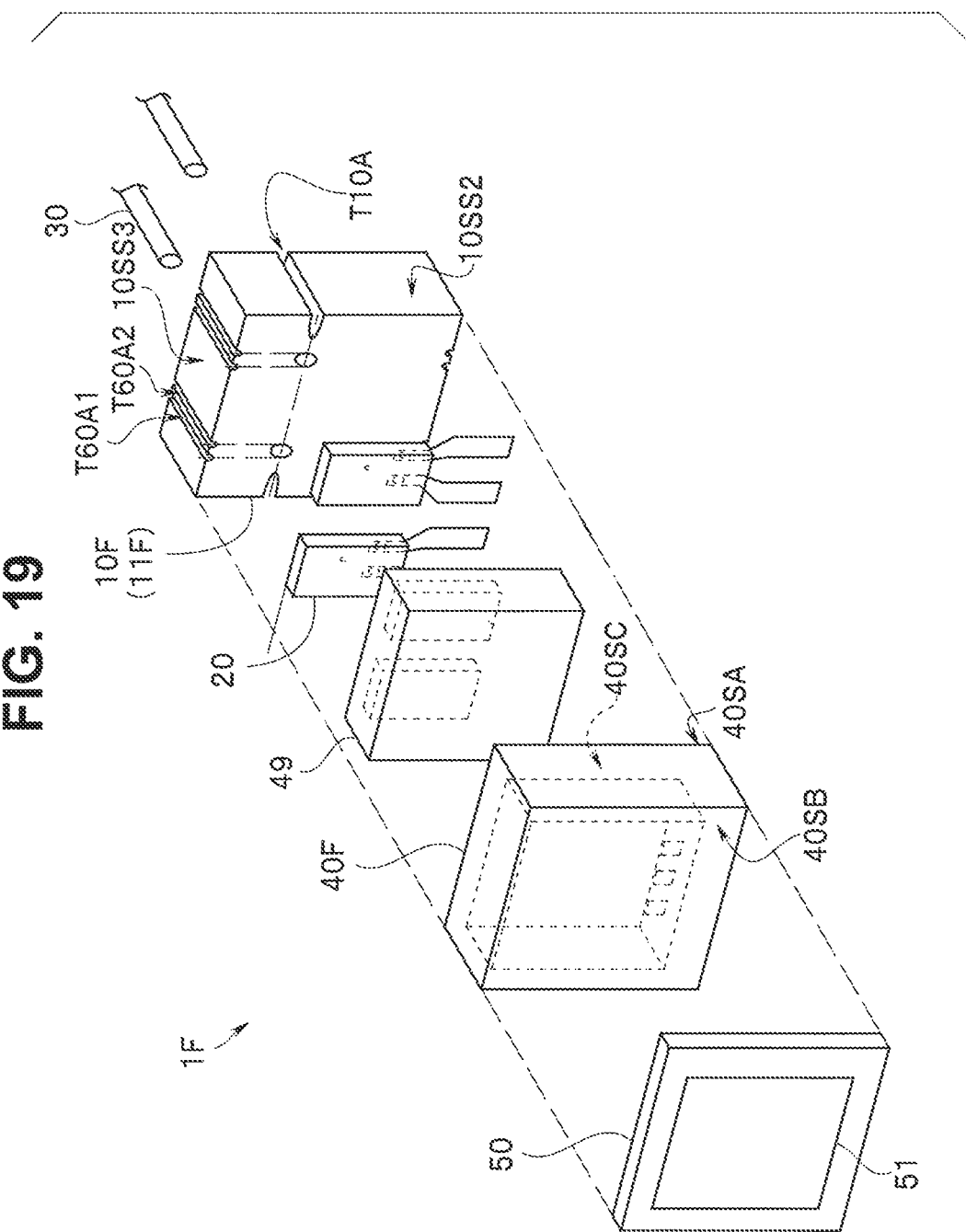
FIG. 19 is a perspective exploded view of an image pickup apparatus in a modification of the fifth embodiment.

In the image pickup apparatus 1F in the modification shown in FIG. 19, sealing resin 49 is filled in the space 40SC formed by a frame section of a wiring board 40F and housing the optical element 20. The sealing resin 49 is injected from the trenches T10A on the second side surface 10SS2 after the wiring board 40F is bonded to a ferrule 10F.

In other words, in a manufacturing method for the image pickup apparatus 1F, the ferrule fixing step S40 is a step for bonding the ferrule 10F to the mounting surface 40SA of the solid wiring board 40F including the mounting surface 40SA and the back surface 40SB on the reverse side of the mounting surface 40SA and including the space 40SC in which the optical element 20 is housed. The manufacturing method for the image pickup apparatus 1F further includes, after the ferrule fixing step S40, a resin injecting step for injecting the sealing resin 49 into the space 40SC through the trenches T10A of the ferrule 10F.

In the image pickup apparatus 1F, the trenches T10A also have a function of resin injection holes. Since the sealing resin 49 is filled in the space 40SC of the image pickup apparatus 1F, reliability of the image pickup apparatus 1F is high.

Note that the configurations of the image pickup apparatuses 1 and 1A to 1F may be combined as appropriate or may include a configuration of any one of the other embodiments. For example, in the image pickup apparatus 1E, the insertion holes H10 and the insertion supporting trenches T60 may be tapered. The image pickup apparatuses 1, 1A to 1C, 1E, and 1F may include, like the image pickup apparatus 1D, one optical element 20, one insertion hole H10, and one optical fiber 30 or may include three or more optical elements 20 and the like.

The present invention is not limited to each of the embodiments or the modifications explained above. Various changes, combinations, and applications may be implemented within a range not departing from the gist of the invention.

What is claimed is:

1. An image pickup apparatus for use with an endoscope, the image pickup apparatus comprising:
   an image sensor configured to output an image pickup signal;
   a ferrule having a rectangular parallelepiped including a front surface, a rear surface opposing the front surface, and side surfaces including first, second, third and fourth side surfaces, each of the side surfaces connecting the front and rear surfaces, each of the side surfaces being orthogonal to the front surface, and each adjacent pair of the side surfaces being orthogonal to each other;
   wherein the ferrule further comprising:
     one or more insertion through holes extending in a thickness direction from the front surface to the rear surface,
     a first electrode disposed on the front surface, and
     one or more trenches extending in the thickness direction and being provided on at least two adjacent side surfaces of the first, second, third and fourth side surfaces;
   one or more optical fibers respectively inserted into the one or more insertion holes; and
   one or more optical elements having a light emitting region configured to output an optical signal to the one or more optical fibers, respectively, the one or more optical elements having an external electrode disposed on a light emitting surface and electrically connected to the first electrode, such that the image pickup signal output from the external electrode is input to the first electrode.

2. The image pickup apparatus according to claim 1, wherein one or more of a hole opening on the rear surface of each of the insertion holes and a trench opening on the rear surface of the trench has a tapered shape.

3. The image pickup apparatus according to claim 1, wherein a trench of the one or more trenches formed on one of the at least two adjacent two side surfaces is provided at a position corresponding to where each of the one or more insertion holes is projected onto the one of the at least two adjacent side surfaces.

4. The image pickup apparatus according to claim 1, wherein the one or more trenches are further formed on two parallel side surfaces among the side surfaces, the one or more trenches formed on one of the two parallel side surfaces having a different width and a different depth than the one or more trenches formed on an other of the two parallel side surfaces.

5. The image pickup apparatus according to claim 1, further comprising a wiring board including a mounting surface and a back surface on a reverse side of the mounting surface, a third electrode being disposed on the mounting surface or a protrusion of the mounting surface, wherein
the ferrule includes a second electrode connected to the first electrode on the front surface,
the ferrule is bonded to the mounting surface by an adhesive, and
the second electrode is solder-bonded to the third electrode.

6. The image pickup apparatus according to claim 5, wherein
the one or more trenches include a cutout trench formed on an end side of a first side surface bonded to the mounting surface among the side surfaces, and
the adhesive is disposed in the cutout trench.

7. The image pickup apparatus according to claim 6, wherein
the one or more trenches include a positioning trench formed on the first side surface bonded to the mounting surface among the side surfaces,
a projection is provided on the mounting surface of the wiring board, and
the protrusion is fit with the positioning trench.

8. The image pickup apparatus according to claim 5, wherein
the one or more trenches include a buffer trench formed on the first side surface bonded to the mounting surface among the side surfaces, and
the adhesive is disposed in the buffer trench.

9. The image pickup apparatus according to claim 5, wherein the one or more trenches is formed on a third side surface parallel to the first side surface bonded to the mounting surface among the side surfaces is an alignment trench formed in a position corresponding to a position of the second electrode.

10. The image pickup apparatus according to claim 5, further comprising a cable for transmitting an electric signal, wherein
the one or more trenches include a connection trench formed on the first side surface bonded to the mounting surface among the side surfaces,
a fourth electrode is disposed in a region opposed to the first side surface of the mounting surface,
a connection hole, on an inner surface of which the fourth electrode is provided, is formed by the connection trench and the mounting surface, and
the cable is inserted into the connection hole and bonded to the fourth electrode.

11. The image pickup apparatus according to claim 1, further comprising:
the one or more optical elements comprise a plurality of optical elements; and
the one or more optical fiber comprise a plurality of optical fibers for respectively transmitting respective optical signals outputted by the plurality of optical elements, wherein
the one or more insertion holes comprise a plurality of insertion holes into which the plurality of optical fibers are respectively inserted are provided in the ferrule.

12. The image pickup apparatus according to claim 1, wherein a side surface of the side surfaces parallel to a side surface on which the one or more trenches is formed includes a counter trench in a same position as the one or more trenches.

13. The image pickup apparatus according to claim 1, wherein an inner surface of the one or more trenches is a wall surface of a trench hole formed simultaneously with the one or more insertion holes.

14. The image pickup apparatus according to claim 1, wherein a trench of the one or more trenches formed on each of the at least two adjacent two side surfaces is provided at a position corresponding to where each of the one or more insertion holes is projected onto each of the at least two adjacent side surfaces.

15. An endoscope comprising:
an insertion portion; and
an image pickup apparatus disposed on a distal end portion of the insertion portion, the image pickup apparatus including:
an image sensor configured to output an image pickup signal;
a ferrule having a rectangular parallelepiped including a front surface, a rear surface opposing the front surface, and side surfaces including first, second, third and fourth side surfaces, each of the side surfaces connecting the front and rear surfaces, each of the side surfaces being orthogonal to the front surface, and each adjacent pair of the side surfaces being orthogonal to each other, wherein the ferrule further comprising:
one or more insertion through holes extending in a thickness direction from the front surface to the rear surface,
a first electrode disposed on the front surface, and
one or more trenches extending in the thickness direction and being provided on at least two adjacent side surfaces of the first, second, third and fourth side surfaces;
one or more optical fibers respectively inserted into the one or more insertion holes; and
one or more optical elements having a light emitting region configured to output an optical signal to the one or more optical fibers, respectively, the one or more optical elements having an external electrode disposed on a light emitting surface and electrically connected to the first electrode, such that the image pickup signal output from the external electrode is input to the first electrode.

16. A ferrule for use with an image pickup apparatus of an endoscope, the ferrule comprising:
a ferrule body including a front surface, a rear surface opposing the front surface, and side surfaces including first, second, third and fourth side surfaces, each of the side surfaces connecting the front and rear surfaces, each of the side surfaces being orthogonal to the first side surface, and each adjacent pair of the side surfaces being orthogonal to each other;
wherein the ferrule body further comprising:

one or more insertion through holes extending in a thickness direction from the front surface to the rear surface, a first electrode disposed on the front surface, and one or more trenches extending in the thickness direction and being provided on at least two different side surfaces of the first, second, third and fourth side surface.

17. The ferrule according to claim 16, wherein the at least two different side surfaces comprise at least two adjacent side surfaces.

18. The ferrule according claim 17, wherein the one or more trenches formed on the at least two adjacent side surfaces are provided at positions corresponding to positions where each of the one or more insertion holes is projected onto each of the at least two adjacent side surfaces.

19. The ferrule according claim 16, wherein the one or more trenches are provided at a position on one of the two different side surfaces corresponding to a position where each of the one or more insertion holes is projected onto the one of the at least two adjacent side surfaces.

20. The ferrule according claim 16, wherein the ferrule body has a rectangular parallelepiped shape.

* * * * *